United States Patent
Hamilton

(10) Patent No.: US 10,565,706 B2
(45) Date of Patent: Feb. 18, 2020

(54) METHOD AND APPARATUS FOR TISSUE RECOGNITION

(71) Applicant: KONINKLIJKE PHILIPS N.V., Eindhoven (NL)

(72) Inventor: Peter Hamilton, Belfast (GB)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 139 days.

(21) Appl. No.: 15/761,675

(22) PCT Filed: Sep. 23, 2016

(86) PCT No.: PCT/GB2016/052973
§ 371 (c)(1),
(2) Date: Mar. 20, 2018

(87) PCT Pub. No.: WO2017/051190
PCT Pub. Date: Mar. 30, 2017

(65) Prior Publication Data
US 2018/0350067 A1   Dec. 6, 2018

(30) Foreign Application Priority Data
Sep. 23, 2015 (GB) .................................. 1516871.9

(51) Int. Cl.
*G06K 9/00* (2006.01)
*G06T 7/00* (2017.01)
(Continued)

(52) U.S. Cl.
CPC .......... *G06T 7/0012* (2013.01); *G02B 21/365* (2013.01); *G06K 9/00147* (2013.01);
(Continued)

(58) Field of Classification Search
None
See application file for complete search history.

(56) References Cited

U.S. PATENT DOCUMENTS 7,761,240 B2 * 7/2010 Saidi ................... G06K 9/0014
382/128
9,298,968 B1 * 3/2016 Peljto ................. G06K 9/00127
(Continued)

FOREIGN PATENT DOCUMENTS

WO   2003105675 A2   12/2003
WO   2005027015 A2    3/2005

OTHER PUBLICATIONS

He, Lei et al "Histology Image Analysis for Carcinoma Detection and Grading", Computer Methods and Programs in Biomedic, vol. 107, No. 3, Dec. 2011, pp. 538-556.
(Continued)

*Primary Examiner* — Shervin K Nakhjavan
(74) *Attorney, Agent, or Firm* — Sherry Austin

(57) ABSTRACT

A computer implemented image processing method is disclosed. The method comprises applying a selected filter to image data to identify a subset of the image data that defines a number of discrete spatial regions of the image wherein the discrete spatial regions comprise less than all of the area of the image; selecting, from a data store, a set of quantitative image metrics wherein the quantitative image metrics are selected based on descriptor data indicating tissue type, determining, for each discrete spatial region, a sample region data value for each of the set of quantitative image metrics based on the subset of image data associated with the or each discrete spatial region, using the descriptor data to select, from the data store, at least one comparator set of tissue model data values, wherein each comparator set is associated with a different corresponding comparator tissue structure and each comparator set comprises data values of the set of quantitative image metrics for the corresponding comparator tissue structure; comparing the sample region data value for each discrete region with the at least one comparator set; and in the event that the sample region data (Continued)

value for the or each discrete region matches the comparator set, determining based on an identity of the corresponding comparator tissue structure, whether to further analyse the or each discrete region.

15 Claims, 7 Drawing Sheets

(51) Int. Cl.
    *G02B 21/36*     (2006.01)
    *G01N 1/30*     (2006.01)

(52) U.S. Cl.
    CPC ............. *G01N 1/30* (2013.01); *G06K 9/0014* (2013.01); *G06T 2207/30024* (2013.01)

(56) References Cited

U.S. PATENT DOCUMENTS

| | | | |
|---|---|---|---|
| 2005/0266395 A1 | 12/2005 | Gholap | |
| 2006/0127880 A1* | 6/2006 | Harris | G06K 9/00127 435/4 |
| 2007/0159688 A1 | 7/2007 | Descour | |
| 2012/0115139 A1* | 5/2012 | Kuroda | C12Q 1/6886 435/6.11 |
| 2014/0233826 A1* | 8/2014 | Agaian | G16H 50/30 382/133 |
| 2015/0141278 A1* | 5/2015 | Hollman-Hewgley | G01N 1/30 506/9 |
| 2015/0254493 A1* | 9/2015 | Madabhushi | G06K 9/0014 382/133 |
| 2015/0254494 A1* | 9/2015 | Madabhushi | G06K 9/0014 382/133 |
| 2016/0253817 A1* | 9/2016 | Chen | G06T 7/11 382/133 |
| 2016/0321495 A1* | 11/2016 | Chukka | G06T 7/0012 |

OTHER PUBLICATIONS

Belsare, A.D. "HIstopathological Image Analysis using Image Processing Techiques: An Overview", Signal and Iamge Processing: An International Journal, vol. 3, No. 4, Aug. 2012, pp. 23-36.

* cited by examiner

METHOD AND APPARATUS FOR TISSUE RECOGNITION

CROSS-REFERENCE TO PRIOR APPLICATIONS

This application is the U.S. National Phase application under 35 U.S.C. § 371 of International Application No. PCT/GB2016/052973, filed on Sep. 23, 2016, which claims the benefit of GB 1516871.9, filed on Sep. 23, 2015. These applications are hereby incorporated by reference herein.

FIELD OF INVENTION

The present invention relates to cytological and histological analysis of tissue samples, and more particularly to methods of analysis of microscope images, for example of stained tissue samples, and apparatus therefor. Still more particularly the disclosure relates to the digital image processing of microscope images for the purposes of digital pathology and whole slide imaging.

BACKGROUND

Digital Pathology, which can also be referred to as virtual microscopy or virtual pathology involves managing, analysing and interpreting digital information. The present disclosure relates to the application of methods of "machine vision" and "computerised image understanding" in tissue analysis and cancer detection. It also relates to multiresolution interrogation, and pattern driven analysis (e.g. the patterns in the data drive the processing functions) and selective image processing (reductions in global processing, and the selective application of different image processing function).

The process involves the generation of glass slides and converting these to digital pathology slides using digital pathology solutions. A digital slide scan is then generated which allows for high resolution viewing, interpretation and image analysis of digital pathology images. Growth in digital pathology solutions has totally transformed how research labs manage and interpret glass slides, with analysis and interpretation of histological images now conducted on a computer screen.

Gaining momentum globally, digital pathology is being used across health and pharmaceutical sectors, education and contract research organisations. With wide ranging applications the realised benefits of this sophisticated technology have encourage high growth in the market for digital pathology solutions, which by 2020 is estimated to be worth $5.7 billion.

Whole slide imaging and digital pathology are significant ongoing fields of research. The methods in the present case contribute new developments in this field of technology. Cytonuclear analysis involves the automated recognition of cell boundaries and nuclear boundaries within Haematoxylin and Eosin stained tissue samples. This may be achieved by a process of colour deconvolution, and may be processed further to identify biological objects such as nuclei. In general, nuclei are the most easily identifiable components in Haematoxylin and Eosin stained tissue samples. This cytonuclear analysis is a key tool in providing accurate diagnoses.

The ability to provide accurate diagnosis is critical to the provision of healthcare. Biopsies to identify the presence of diseases such as cancer are a useful tool in such diagnosis. They may also enable predictions to be made about both future development of disease in a patient, and patient response to treatment in the context of precision or personalised medicine. Accurate prognostic assessment is also critically important, because it enables action to be taken to counteract further development of disease. Microscope images of tissue samples have been used for these purposes for many years.

Large numbers of microscope imaging systems, each with their own particular characteristics, have been developed for this purpose. Whole slide imaging systems obtain digital images of entire microscope slides by scanning the field of view of a microscope across a macroscopic tissue sample to obtain a series of digital images. The resulting digital images can then be concatenated together to provide a single image, or image set, which describes the entire microscope slide. Partial images of slides can also be obtained by the same approach.

Pathologists involved in making diagnoses based on these kinds of images may rely on qualitative judgements. Such judgements may be based on their scientific knowledge and also on personal experience. This is necessarily a subjective process. As a result diagnoses, prognostic assessments, predictive assessments, the selection of patients for clinical trials, and the discovery and validation of new biomarkers are not always reproducible—different pathologists may make different judgements based on identical images of tissue samples.

In making diagnostic judgements, the pathologist's task is made still more difficult because large tissue samples may be involved. In such cases many tens, or even hundreds of microscope images may need to be analysed from a single patient, and in some cases, it may be necessary to review regions of these multiple microscope images at multiple resolutions. This is particularly true where multiple tissue biopsies have been taken from a relatively large area of the body such as the prostate. These issues compound the problem of reproducibility because two different pathologists assessing the same patient's tissue sample may take into account features of different areas of different images of the same tissue sample.

The conditions under which a tissue sample was obtained, and the treatment of that sample before it was imaged (for example in terms of the concentration of stain applied to it), the imaging system used to acquire the image, and the presence of image artefacts may all cause variations between images. Although painstaking analysis is required, human pathologists are at least able intuitively to make allowances for such confounds. The subjective nature of assessment by human pathologists therefore, whilst problematic, at least provides one way to address these problems of inter-image variability. This need for intuitive judgement prevents straightforward automation of diagnostic and prognostic assessment of microscope images.

There are still further obstacles to overcome.

SUMMARY OF INVENTION

Aspects and examples of the invention are set out in the claims and aim to address technical problems such as those outlined above. Aspects and examples of the invention are also described herein.

BRIEF DESCRIPTION OF DRAWINGS

Embodiments of the disclosure will now be described, by way of example only with reference to the accompanying drawings, in which.

In the drawings like reference numerals are used to refer to like elements.

SPECIFIC DESCRIPTION

Disclosed herein is an image analysis and tissue recognition system which can carry out analysis of Haematoxylin and Eosin stained images, and is able to identify different tissue types based on their complex patterns, different types of diseases within a particular tissue type, and recognition of different tissue structures in health and disease captured in these images, based on anatomical knowledge, and can analyse the content of the image using mathematical operators and comparator data.

Embodiments of the disclosure relate to image processing methods and apparatus which aim to enable objective comparisons between images, and aim to improve the computational efficiency of automated diagnoses, and both predictive and prognostic assessments based on microscope images. This is done by analysing the image and excluding sections of the image which are not of interest, and then performing further analysis on the sections of the image which are of interest.

To accomplish this, a computer obtains descriptor data which indicates the type of image data that the image contains and, based upon the descriptor data, selects an image operator which is configured to identify structures in that image data. For example this image operator may comprise a thresholding operation, or an operation to identify data in the image which has a spatial length scale in a selected range. The computer applies the image operator to the image, to identify a subset of image data which is formed of a number of discrete spatial regions of the image. These discrete spatial regions comprise less than all of the area of the image. The computer also selects a set of quantitative image metrics based upon the descriptor data, and determines sample region data for the quantitative image metrics based upon the image data in each discrete spatial region of the original image. This sample region data comprises values of the selected quantitative image metrics. It is then compared against comparator data values of those same quantitative image metrics. Based on the result of the comparison, the computer determines whether the or each discrete spatial region of the image is to be analysed further.

The discrete spatial regions, regions of interest, which form the basis of this analysis may be recombined once they have been identified to provide a composite image—or a map of the tissue identifying which areas of tissue correspond to which types of tissue structure.

Further analysis of a region of interest may comprise modifying the image operator, or applying a different image operator to that region, and then attempting (or reattempting) the classification of that image region. A variety of such embodiments are disclosed herein.

Figure 1:
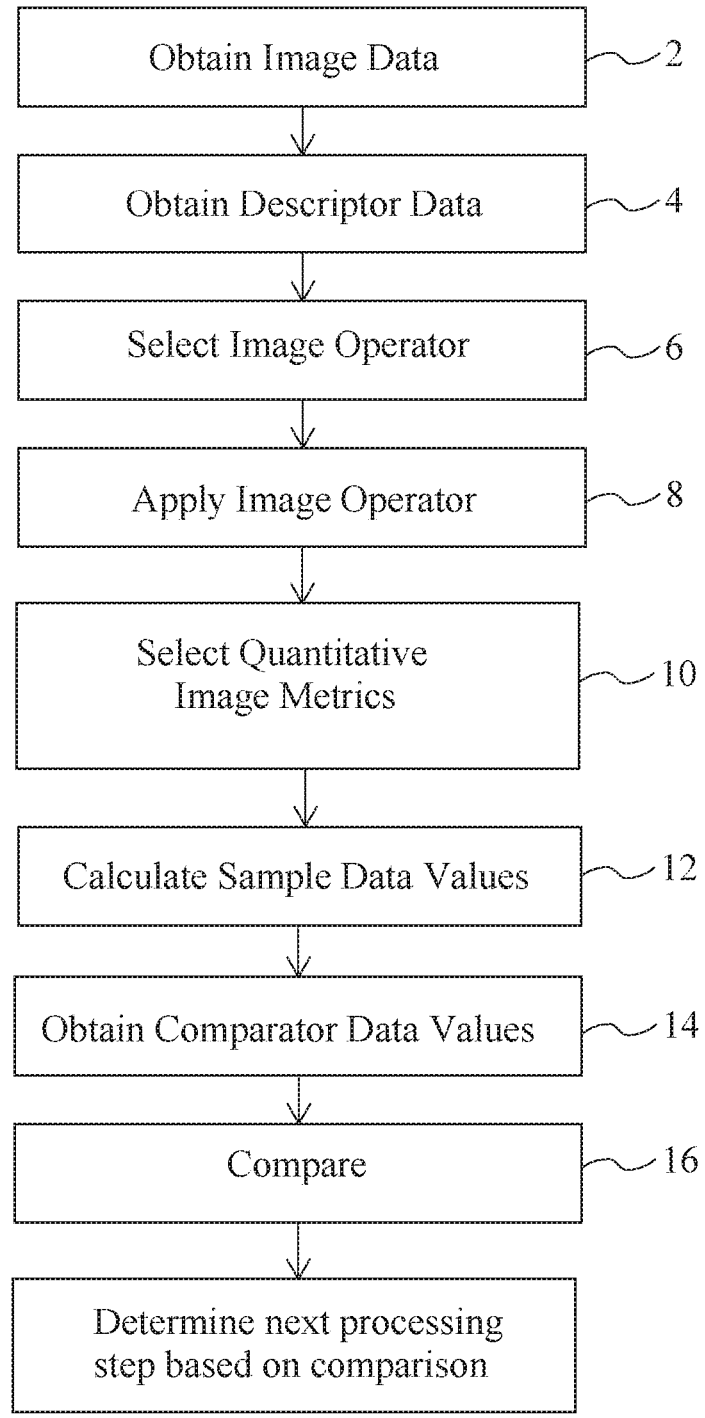
FIG. 1 includes a flow chart indicating a method of obtaining and analysing image data.

FIG. 1 illustrates one such computer implemented method. In this method, the computer first obtains 2 microscope image data for analysis. This microscope image data may comprise whole slide images. The image data often defines a microscope slide image of a haematoxylin and eosin stained tissue sample, but the slides may also be stained using saffron (as in HES staining). The data itself may be obtained from data storage in the computer's memory and/or may be received over a network. This data may also be obtained from a tissue sample by a microscope imaging system as part of the method and communicated directly to the computer. The image data may originate from a whole slide imaging system.

The memory of the computer comprises an association, such as a look up table, which links a plurality of items of descriptor data to a corresponding plurality of sets of quantitative image metrics. Each item of descriptor data comprises a machine readable identifier of a tissue type. The association links each item of descriptor data to a set (or sets) of quantitative image metrics associated with that tissue type. This enables the correct image metrics to be retrieved from memory for the analysis of any given tissue type (as identified by the descriptor data). Each item of descriptor data is also associated with at least one corresponding set of comparator data values. Each set of comparator data values indicate the values of quantitative image metrics obtained from a tissue structure known (or expected) to be found in the type of tissue identified by the corresponding descriptor.

For example, the descriptor data may identify tissue types such as breast tissue, prostate tissue, lung tissue, pancreatic tissue and other types of tissue. It will be appreciated in the context of the present disclosure that each of these tissue types may comprise different types of structures. Accordingly, more than one comparator data set is generally associated with each descriptor. Each of these comparator data sets describes a different tissue structure known (or expected) to exist in that tissue type.

It will therefore be appreciated that each descriptor is associated in the computer memory with (a) a set of quantitative image metrics and (b) sets of comparator data values of those image metrics where each set of comparator values describes a different structure in that tissue type. For example, the descriptor for breast tissue may be associated with a set of quantitative image metrics, and corresponding comparator data values of those metrics for each of: fat tissue, blood vessels, ducts, lobules, LCIS (lobular carcinoma in situ), DCIS (ductal carcinoma in situ), and perhaps one or more other types of tumour.

This can enable particular structures in particular tissue types to be identified by (1) calculating the relevant image metrics and (2) comparing those metrics with the comparator data values to find a match. This can enable distinctions to be drawn between different structures in a particular tissue type. The comparator data may, dependent upon the tissue type identified by the descriptor data, include comparator data for one or more of: necrosis, inflammatory cells, mitoses, lobules, other anatomical structures, PIN (prostatic intraepithelial neoplasia), colorectal dysplasia, invasive cancer and one or more other types of tumour. A further distinction may be drawn between pre-cancerous cells and cancerous cells, and pre-cancerous cells may, for instance, have different comparator data from pre-cancerous and cancerous cells.

Each of these comparator sets comprises data values for a set of quantitative image metrics. For example, these may include one or more items selected from the following list: cell nuclear area ($\mu m^2$), nuclear shape factors (e.g. ratio of nuclear area to perimeter length), cell area ($\mu m^2$), cell shape factors such as ratio of cell area to cell perimeter length, numbers of identified cell populations, cell density (based upon the relative number of objects per unit area), optical density, the grey values of RGB deconvoluted channels, nuclear texture features, glandular area ($\mu m^2$), glandular shape, nuclear stratification, Delauney triangulation metrics, and/or the number of specific tissue objects in the image for the or each corresponding comparator tissue structure.

The descriptor data is then obtained 4 by the computer, for example it may be provided with the microscope image data or it may be stored in memory with that image data.

Then, the descriptor data is used to select 6, from data storage in the computer memory, an image operator which may be configured to identify image data having selected spatial characteristics, for example a spatial length scale in a selected range. Examples of image operators include spatial filters and feature extraction operators such as morphological filters (examples of which are set out in greater detail below). Examples of spatial filters include frequency domain operators such as spatial band pass filters, for example low pass filters, for example a Gaussian filter. It will be appreciated in the context of the present disclosure that such operators may be applied in the frequency domain, for example by transforming the image data into the frequency domain, applying the operator, and then transforming the filtered image data back into the image domain. Examples of spatial filters also include image kernels, such as smoothing kernels, which may be applied in the image domain.

The image operator is selected 6 by the computer, based upon the descriptor data, and based on the type of structure within the tissue type associated with that descriptor which is to be identified first. For example, a plurality of image operators may be stored in memory associated with each item of descriptor data. Each of these image operators may be configured to enhance image regions having length scale/shape characteristics that correspond to structures known (or expected) to be found in that tissue type.

Some examples of image operator may be configured to identify features of a particular size, e.g. those which vary on a spatial length scale which falls within a selected range. This length scale may be chosen based upon the type of structure which is to be identified (e.g. a duct or lobule in the context of breast tissue) or based on the type of cells in the tissue type as identified by the descriptor data.

One example of an image operator which may be used for this purpose is a morphological filter. The size and shape of the structuring element of such a morphological filter may be selected based upon the descriptor data. For example, each item of descriptor data may be associated with one or more different morphological filters. The morphological filter may be configured to provide an erosion operation, a dilation operation, or may include a combination of erosion and dilation operations—such as an 'opening' operation, which is an erosion operation followed by a dilation operation, or a 'closing' operation, which is a dilation operation followed by an erosion operation. The use of such image operators and operations may enable the resolution and identification of key tissue structures that may exist in a tissue sample. Further, it may also provide a series of metrics that may be used to identify the different tissue and cell structures. These may in turn be used to differentiate different pathologies in tissue samples. These pathologies may include tumours or abnormal cells which may, for example, be benign, precancer, and/or cancer cells. By way of example, if breast cancer is present, the cell nuclei may be much larger, irregular, and more dense. Further, low-grade DCIS may exhibit rounded, regular to mildly-irregular nuclei up to around two or three times the size of a red blood cell. High-grade DCIS may exhibit irregularly-shaped nuclei which may be at least three times the size of a red blood cell. DCIS patterns may include 'cribiform', 'macrocapillary', and/or 'solid', and it is possible to describe all of these patterns quantitatively and/or numerically.

Whichever image operator is chosen, the computer then applies 8 the image operator to the microscope image data to obtain filtered image data. The filtered image data may comprise regions in which the image intensity has been reduced because the structures in that region of the image do not have the spatial characteristics selected by the image operator. Accordingly, by application of an intensity threshold to the filtered image data a number of discrete spatial regions of the microscope image data can be identified. These discrete spatial regions may have spatial characteristics (e.g. size and/or shape) that, in the context of that tissue type, might imply that they could be to one or more possible candidate structures. For instance, a first image operator may comprise a morphological filter having a structuring element adapted to select structures of a size and shape corresponding to a breast tissue duct, or ductal carcinoma in situ, and to suppress other structures. It will be appreciated that references to ducts and DCIS are merely an example, and different image operators may be applied to identify different tissue structures such as fat tissue, blood vessels, stromal cells, epithelium, glands, ducts, lobules, tumor patterns and one or more types of tumour. It will also be appreciated that the image operator may itself comprise a series of component operators—for example a first component operator may comprise a morphological filter configured to identify and bridge together (e.g. to merge) contiguous image regions which comprise epithelial cells: a second component operator may compare the size and/or shape of the bridged contiguous image regions with size and shape ranges for selected known structures such as ducts. In these embodiments, the filtered image data may comprise the regions of the image which match these selected known structures, other non-matching regions of image data may be excluded from the filtered image data.

After application of the first image operator the computer then selects 10 a relevant set of quantitative image metrics from memory—e.g. based on the descriptor data, and the size/shape characteristics of the first image operator. This set of quantitative image metrics comprises metrics for structures of that size/shape known (or expected) to be found in that tissue type. This set of quantitative image metrics may include one or more items selected from the list comprising: a frequency domain metric, a texture metric, a Gray-Level Co-Occurrence Matrix ('GLCM') metric, an optical density, a colour, or any other suitable metric. These metrics may be used to determine a signature, rather in the manner of a fingerprint, for the or each discrete spatial region.

The set of quantitative image metrics may comprise a metric that is based upon an optical density in the or each discrete region. As will be appreciated in the context of the present disclosure, optical density describes the transmission of light through the or each discrete region, and may be defined as the negative of the logarithm (base 10) of the fraction of incident light that is transmitted through a sample, e.g. where the transmission varies between 0 and 1.

By comparison with comparator data values, the level of the transmission of the light (and therefore the optical density) of the or each discrete region may be used to obtain information regarding the content of the or each discrete region.

The set of quantitative image metrics may comprise a metric that is based upon spatial frequency data in a selected range of spatial frequencies in the or each discrete region. Spatial frequency data may be obtained by performing a frequency transform (such as a Laplace or Fourier type transform, for example a DFT, for example an FFT, for example a DOT). The resultant spatial frequency data may be used to identify spatial frequencies present in the image data in the or each discrete region. This spatial frequency data can then in turn be used to obtain information regarding the content of the or each discrete region by comparing the spatial frequency data values obtained from the or each region with comparator data values associated with the tissue type (as identified by the descriptor data). The inventors in the present case have appreciated that, whilst normal cells and cancerous cells may show relatively subtle differences in their geometric structures in the spatial domain, these relatively subtle differences may be more effectively measured in the frequency domain, in which more precise measurements can be extracted to characterise different tissue patterns. Furthermore, frequency domain analysis of the image may enable information which is not visible in the spatial domain to be detected, providing more effective and accurate image analysis.

The set of quantitative image metrics may comprise a metric that is based upon the texture of the or each discrete region may be analysed, so as detect particular characteristics that may appear, and/or such that repeating patterns or otherwise may be detected. By way of example, Haralick texture features and/or co-occurrence matrices may be used to analyse the texture of the or each discrete region to be analysed. It is to be understood, however, that any suitable method may be used to quantitatively describe the underlying tissue pattern in the or each discrete region.

The computer then calculates 12, for each discrete spatial region, at least one sample data value, by applying the quantitative image metrics to the image data in said discrete spatial region. The set of quantitative image metrics may include one metric, such as those identified above, or indeed may include more than one metric. The or each quantitative image metric may be applied in parallel, or in a predefined sequence, or they may be applied in a hierarchical (pattern driven) nature as explained below with reference to FIG. 2.

The computer uses 14 the descriptor data to obtain the set of (or sets of) comparator data values (e.g. values of these quantitative image metrics) from the computer memory. For example the computer memory may comprise a look-up table or other memory reference structure which enables the selection of the comparator data values, using the descriptor data as an index. One examples of such a data structure is explained below with reference to the storage of tissue data in FIG. 7. As explained there, the comparator set may include comparator data values for known comparator structures. Such structures may, for example, include a carcinoma-in-situ a gland, a duct, a lobule, fat tissue, or the like, or other artefacts or structures which may be of interest. The comparator data values may have been obtained previously by evaluating the quantitative image metrics in samples of tissue known to contain one of these known comparator structures.

The computer then compares 16 the data values obtained from the sample image to at least one of these sets of comparator data values. These comparator data sets may define a number of features which may, for instance, include different tolerance ranges. If the data values obtained from the sample image fall within this tolerance range or set of tolerance ranges, the sample data may then be classified as matching the comparator data structure associated with that data set. This comparison may be achieved using by simple numeric comparison of each metric against the model in the comparator data set. Alternatively or in combination, it may also be carried out in a multivariate setting, and/or a similarity index for example a Jaccard coefficient and/or Euclidean distance may be calculated.

In the event that the sample data values match comparator data values from a known type of structure in the tissue type, the region from which those sample data values were calculated is identified as being that type of structure. Based upon the above operations, some parts of the sample image data may be identified as belonging to one or more of the tissue structures described by the comparator sets. One or more of these comparator sets may correspond to tissue types which are known to look similar to certain types of cancer, or to be pre-cancerous. Examples of such tissue structures include LOS and DOS in breast tissue, but other such examples exist. In the event that the computer identifies one of these selected types of tissue in one or more of the discrete spatial regions, the computer may then determine 18 whether to analyse the or each discrete spatial region further.

Those discrete spatial regions which are determined 18 as to be analysed further may have subsequent processing steps applied thereto. Those discrete spatial regions which are not to be analysed further may be excluded from subsequent analysis of the image data. This can enable high resolution, or computationally intensive identification algorithms to be applied only to image data which is not amenable to unambiguous identification by less computationally intensive approaches. Examples of such algorithms are described below with reference to FIG. 7.

Figure 2:
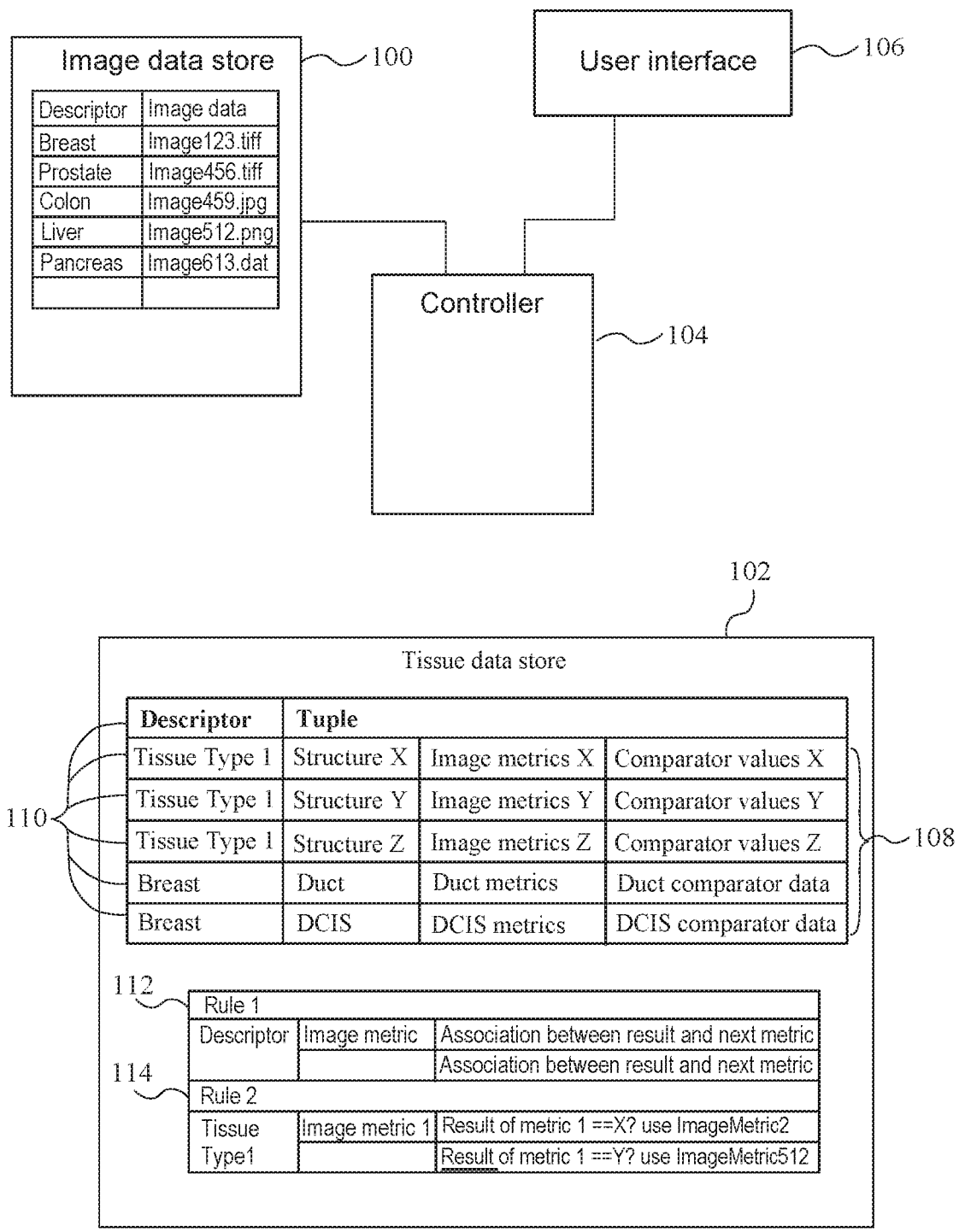
FIG. 2 is a functional block diagram of an image processing apparatus.

FIG. 2 illustrates an apparatus configured to perform a method of pattern driven analysis—that is to say patterns and features of images of the tissue drive the processing functions. To this end, the apparatus illustrated in FIG. 2 is configured to apply a series of quantitative image metrics in a hierarchical fashion—that is to say in a sequence that is selected based on the result of at least one preceding metric(s) in that sequence. It will be appreciated that this is a somewhat complex process, and so in the interests of clarity—a simple example is explained here, but further developments of this principle are envisaged and disclosed herein.

As a first example to explain this pattern driven approach we note that it may be applied to the discrete regions of image data identified during the analysis explained above with reference to FIG. 1. It will be appreciated however that it may be applied independently of that method, for example to other selected parts of images, or to the entirety of an image.

This first example of a hierarchical approach may proceed as follows: a first quantitative image metric is applied to the image data to obtain a result, and a second quantitative image metric is then selected based on that result. This second quantitative image metric is then applied to the image data, and a third quantitative image metric is selected based on the result of applying the second quantitative image metric and perhaps also based on the result of the first quantitative image metric. At each stage, the results obtained are compared with comparator data to determine whether the results (or sequence of results) match the comparator data.

In the event that the results do match, then based on this match, the image data can be associated with a tissue structure known (or expected) to be found in that type of tissue (as identified by the descriptor data). This process can continue through a series of metrics until the results match comparator values giving the signature of a known tissue structure.

The embodiment illustrated in FIG. 2 comprises an image data store 100, a tissue data store 102, a controller 104, and a user interface 106. The controller 104 is coupled to communicate data to and from each of the image data store 100, the tissue data store, and the user interface.

The image data store 100 and the tissue data store both comprise volatile and/or non-volatile data memory for storage and retrieval of digital image data and a data interface to enable data to be read from and written to that memory. Each is coupled to the controller 104 to enable the controller 104 to obtain image data from the image data store 100, and to obtain tissue data such as quantitative image metrics and comparator data from the tissue data store 102. The image data store 100 is also configured to store, for each item of image data, a corresponding descriptor of the tissue type from which that image originates. The descriptors each comprise a label indicating tissue type. Examples of such tissue types include breast tissue, prostate tissue, lung tissue, pancreatic tissue and other types of tissue.

The tissue data store 102 stores, for each descriptor 110, a set of tuples 108. Each tuple provides an association between (a) a structure known (or expected) to be found in the tissue type identified by the descriptor, (b) a set of quantitative image metrics, and (c) a set of comparator data values indicating expected values of those image metrics in that structure. The tissue data store 102 also stores a set of rules 112, 114 configured to cause the controller 104 to apply the quantitative image metrics in an adaptive, selected, sequence—a pattern driven sequence. The rules 112, 114 each define, for each descriptor, a first quantitative image metric that is to be applied to image data having that descriptor. The rules also define an association between each of at least two stored result values (or ranges of result values) of that image metric and each of at least two further quantitative image metrics. Although only two rules are illustrated in FIG. 2 it will be appreciated that this is merely exemplary, and a greater number of rules may be provided.

The controller 104 comprises processing logic, configured to read and write data to and from storage in the image data store 100 and the tissue data store 102. The controller 104 is configured to apply quantitative image metrics to image data obtained from the image data store 100. The processes for applying these quantitative image metrics may be expressed in firmware that is loaded into the controller 104, or it may be hard wired in logic circuits of the controller 104, or they may be provided by a mixture of firmware, hardware and software configuration. The controller 104 is also configured to apply these quantitative image metrics according to a sequence defined by the rules stored in the tissue data store 102. In particular, the controller 104 is configured to select a rule from the tissue data store 102 using the descriptor, and then to apply the quantitative image metric that is provided by that rule to the image data. The controller 104 can then compare the result obtained from applying that quantitative image metric to the image data to the stored result values (or ranges of values) in that rule, and select the next metric to be applied based on that comparison as defined by the rule—e.g. based on the association between the stored result values and the at least two further quantitative image metrics that make up the rule. The controller 104 is therefore operable to obtain for the image data (e.g. corresponding to a sub-region or part of a larger image) a series of result values, each associated with a different quantitative image metric. This series of values can provide a signature which can be compared against comparator data, such as that stored in the tuples. The controller 104 is configured to use the result of this comparison to predict an identity of the structure(s) shown in the image data.

In operation, the image data and its accompanying descriptor are read from the image data store 100 by the controller 104. The controller 104 then uses the descriptor to select the relevant rule from the tissue data store 102 and evaluates the quantitative image metric specified by that rule for the image data. The controller 104 then compares the result of evaluating that quantitative image metric with the stored result values (or ranges) specified in the rule. Accordingly, the next quantitative image metric is identified based on this comparison.

The controller 104 then obtains the next rule by choosing the rule from the tissue data store 102 which is associated with this next quantitative image metric and the descriptor which accompanied the image data. The quantitative image metric specified by this next rule is evaluated for the image data, and the result or results of evaluating this metric are then compared with the stored result values (or ranges) specified in the rule.

This process of selecting the next metric, identifying the next relevant rule, evaluating that next metric, and using the rule and the result value of that metric to select yet another next metric can be repeated. At each iteration (e.g. after evaluation of each metric) the result or series of results can be compared with comparator data such as the comparator data stored in the tuples of the tissue data store 102. In the event that the result or series of results match a set of comparator data in a given tuple, the controller 104 can indicate that the image data is associated with the structure identified in that tuple.

Figure 3:
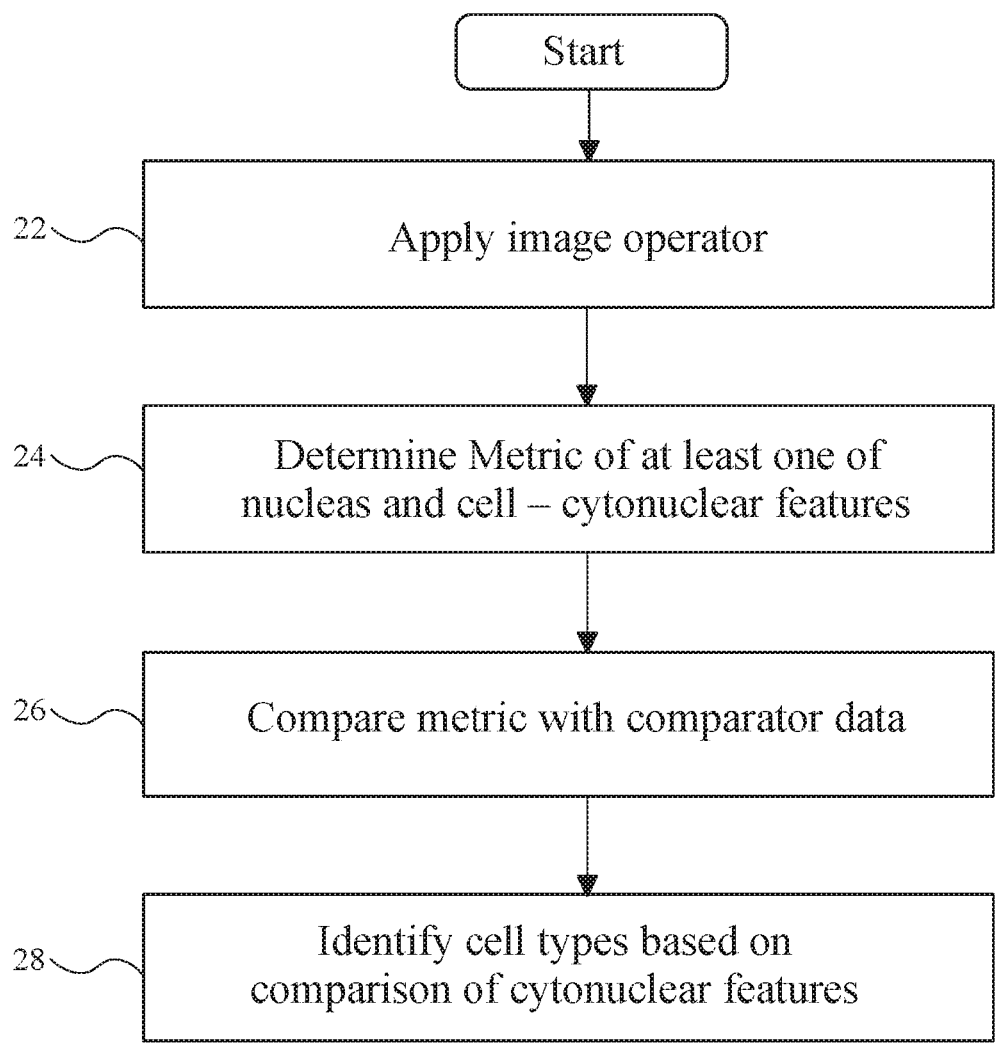
FIG. 3 illustrates a flow chart indicating a method of analysing image data.

FIG. 3 shows further method steps which may also be employed to analyse the discrete spatial regions further. This method of analysis may be directed specifically to the identification of cytonuclear features—that is to say features related to the size and shape characteristics of cell nuclei, and cell boundaries (e.g. the cell membrane).

In the method illustrated in FIG. 3, the computer applies 22 a further image operator to the image data in each discrete spatial region identified as being desirable for further analysis. This further image operator may comprise a morphological filter having a structuring element configured to identify cell nuclei—for example it may have a structuring element having a shape selected to identify cell nuclei—e.g. the structuring element may be rounded, for example elliptical, for example circular. The size of the structuring element may be selected to identify cell nuclei, for example it may have a width of less than 20 micron, for example less than 10 micron. The specific shape and size of this structuring element may be based upon the descriptor data. For example it may be based on size and shape characteristics of types of cell nuclei known (or expected) to be present in the image data identified by that descriptor. The selection may also be based on the structure associated with the comparator data found to match the or each discrete region in the method described above with reference to FIG. 1. It will be appreciated that, although this further image operator is described here as comprising a morphological filter—other image operations may also be used; and this further image operator may itself comprise a series of operations such as spatial filtering, thresholding, and other operations.

Although this operation or series of operations may vary widely, in this embodiment, the key requirement is that this further image operator is adapted to provide cell nuclei data identifying the locations of cell nuclei in the image data based on the size and/or shape characteristics of those nuclei.

The computer then determines 24 the width of the cell nuclei identified by the cell nuclei data. The computer also determines the area occupied by these cell nuclei, and may also determine the length of its boundary. This enables the computer to determine a metric of at least one of: the nuclear shape, its area, its shape factor (e.g. the ratio of its boundary length (or the square of that length) to its area). These metrics are merely examples, and other metrics may be used.

The computer may also use the cell nuclei data to determine a metric of at least one of: a density, a chromatin texture, and nucleoli features. These metrics are merely examples, and other metrics may be used. This metric can then be compared 26 with comparator data to determine 28 whether it is likely that the at least one discrete region may comprise cancerous cells. For example—in the event that highly irregular shaped cell nuclei are identified, this may be used as an indication that the tissue in the discrete region analysed may warrant further inspection—for example by a human operator.

In addition, or as an alternative, to the determination step 24 the computer may also determine the shape and/or size of cell boundaries in the image data. To achieve this, a further image operator configured to identify cell boundaries is applied to the image data. Examples of image operators configured to identify cell boundaries include watershedding algorithms. The output of this further image operator is cell boundary data identifying the locations of cell boundaries. The computer can then use the locations of the cell boundaries in the image data to determine the length of these cell boundaries, and the size of the areas they enclose, amongst other cellular characteristics such as its shape factor.

The computer can then compare 26 the data describing the cytonuclear features of the image data analysed with this method to characteristics of known tissue types and structures. For example, the computer may store one or more sets of cytonuclear comparator data indicating expected ranges of one or more of: cell area, cell shape factor, the ratio of cell area to nuclear area, nuclear shape factor, and nuclear area. The computer may also store an association between these sets of cytonuclear comparator data and cells found in particular tissue structures such as: healthy tissue structures, and pre-cancerous structures and/or cancerous structures. This may enable the computer to identify 28 based on this comparison, one or more of the types of cells in the image data.

Furthermore, the computer can apply the method described above to a plurality of images, and to a number of individual regions of those images. In these embodiments the computer stores, in memory, an association between each of the images and/or each of those regions and a score that is based on (a) the descriptor data indicating the tissue type from which the tissue sample originated, and/or (b) the match between those images or regions and the comparator data sets (for example the statistical confidence level of such a match). The computer then selects a sequence in which to present the slide images to a human operator based on that score. The computer may also highlight particular regions of the images based on the score associated with those image regions.

A tissue sample contained within image data may include a number of pathologies, which may, for example, comprise, consist of, or consist entirely of benign cells, pre-cancer cells and/or cancerous cells in the same image.

In order to analyse these pathologies and identify the pathologies contained therein, the computer may, in an example, apply image processing methods across the image data to identify glands, measure those glands, identify the glands as, for example, DCIS (based on their metrics), and then may subsequently exclude those glandular regions from future analysis. The image data may then be processed yet further with a separate set of image processing methods in order to analyse the remainder of the image.

The image data may include a multitude of normal components and/or structures, such as cells, ducts, and/or the like, and a number of non-normal components and/or structures which, for example, may include pre-cancerous and/or cancerous cells. These normal and non-normal components and/or structures may be combined in a range of complex and variable patterns. The image analysis techniques described herein may enable an effective and efficient decombination and un-mixing of such components and/or structures and subsequent analysis thereof.

The analysis of these normal and non-normal components and/or structures allows for a "map" of these regions across the image to be generated. Such a map may enable more accurate and diverse diagnosis and analysis to be carried out, and may allow identification, at-a-glance, of areas of tissue contained within image data which may require further analysis.

Figure 4:
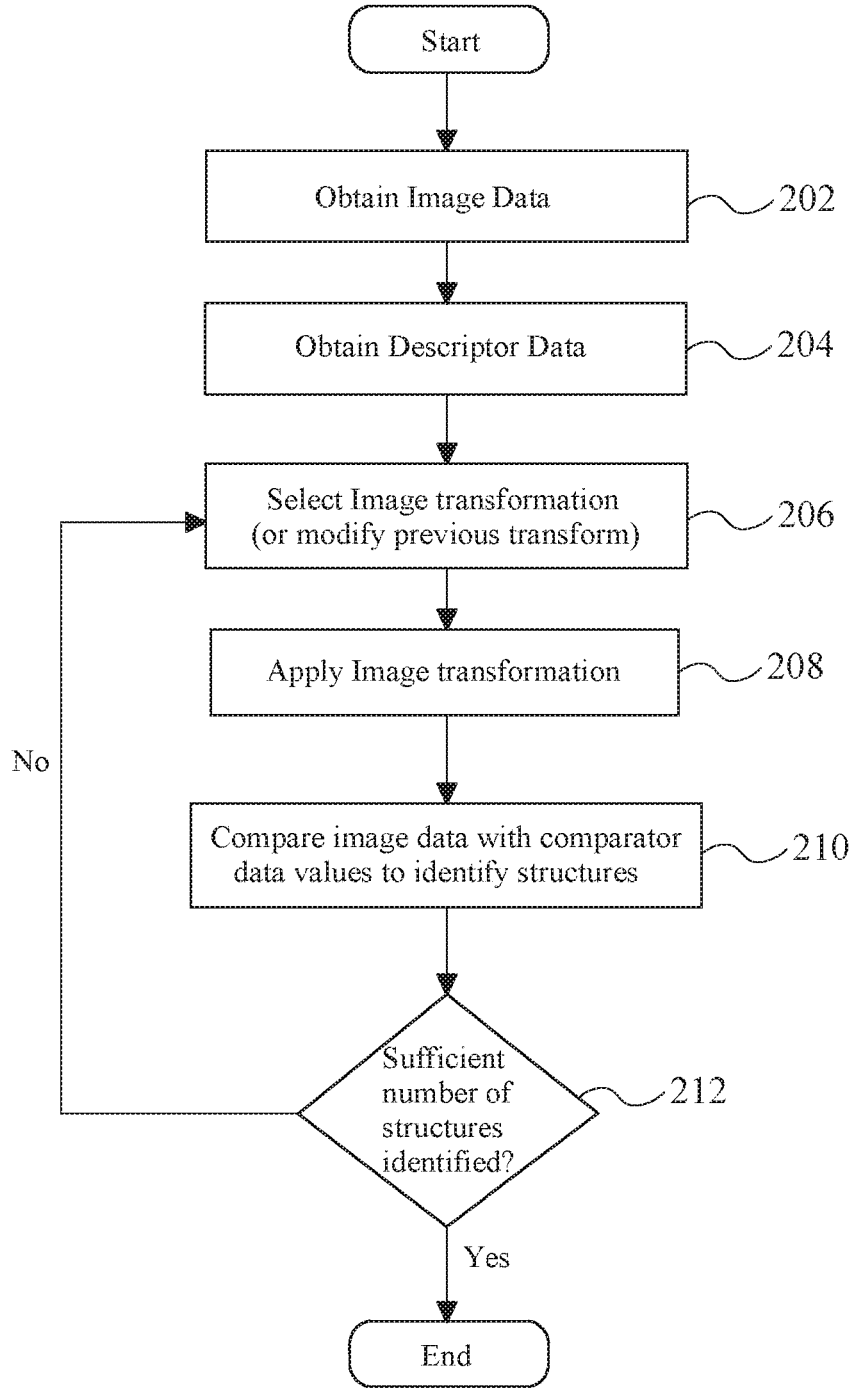
FIG. 4 illustrates a flow chart indicating a further method of analysing image data.

FIG. 4 shows further method steps which may be employed to analyse the image data yet further. In this method a first image data set is obtained 202 from a digital microscope image.

An image transformation is then applied 206 to that first image data to obtain second image data. Structures in this second image data are then classified by comparing them with comparator data to identify them as belonging to one of a number of structures known (or expected) to be found within the tissue type.

In the event that unclassified structures remain in the second image data, the image transformation is modified, and applied 208 again to at least the part of the image data which includes the unclassified structures. This provides a third image data set. Structures in this third image data can then be classified by comparing them with the comparator data.

This process of attempted classification followed by modification of the image transform, followed by reattempted classification of the newly transformed (unclassified) image structures can be repeated until all structures in an image (or an acceptable proportion of those structures) have been properly classified. As set out in connection with the image processing methods above, this approach may be applied alone, in combination, and/or in a hierarchical nature. The further image analysis techniques may be selected based upon the tissue type stored in the descriptor data, and when applied in combination and/or in a hierarchical nature, these further image analysis techniques may be applied in a predetermined order, which may be based upon the tissue type stored in the descriptor data. Further, as set out above, a hierarchical application of these further image analysis techniques may be applied across images at a number of resolutions.

In a similar fashion to the method set out above, the computer obtains 202 microscope image data for analysis, and then obtains 204 descriptor data, which may be provided with the microscope image data that indicates a type of tissue from which the tissue sample originates.

The descriptor data may then be used to select 206 from data storage in the computer memory an image transformation. A description of examples of such image transformations is set out below. The image transformation is applied 208 to obtain first transformed image data.

The computer then uses the descriptor data to obtain a set of (or sets of) comparator data values (e.g. values of these quantitative image metrics) from the computer memory. The first transformed image data is then compared 210 with this comparator data to identify structures in the first transformed image data. The computer then determines 212 whether a sufficient number of structures have been identified (e.g. whether more than a threshold number, or proportion, of structures remain unidentified). In the event that an insufficient number of structures have been identified, the computer returns to step 206 and either (a) select a new image transformation or (b) modifies the previous transformation. This new transformation is then applied 208 and the steps 210 and 212 can be repeated to determine whether yet a further transformation needs to be applied.

FIG. 4 is an example of a method which can be applied to provide a map of a microscope slide image of a haematoxylin and eosin stained tissue sample. Other examples of such methods may be used.

Such methods include selecting an image operation configured to transform the image data, and then applying the selected image operation to the image data to identify a number of discrete spatial regions of the image. To identify these regions of interest (ROIs) quantitative image metrics (such as any one or more of such metrics described herein) can then be applied to the ROIs. This provides sample region data values for each ROI (discrete spatial region), which can be compared with at least one set of comparator data in an attempt to identify that region.

In the event that the sample region data value matches a comparator set, a next region can be tested by attempting to match it against comparator data. By treating each area of an image in this way a map of the image can be assembled in which each area (or at least a number of areas) of the image are labelled as belonging to a particular tissue structure. This can be used to provide a composite digital image of the tissue.

Figure 5:
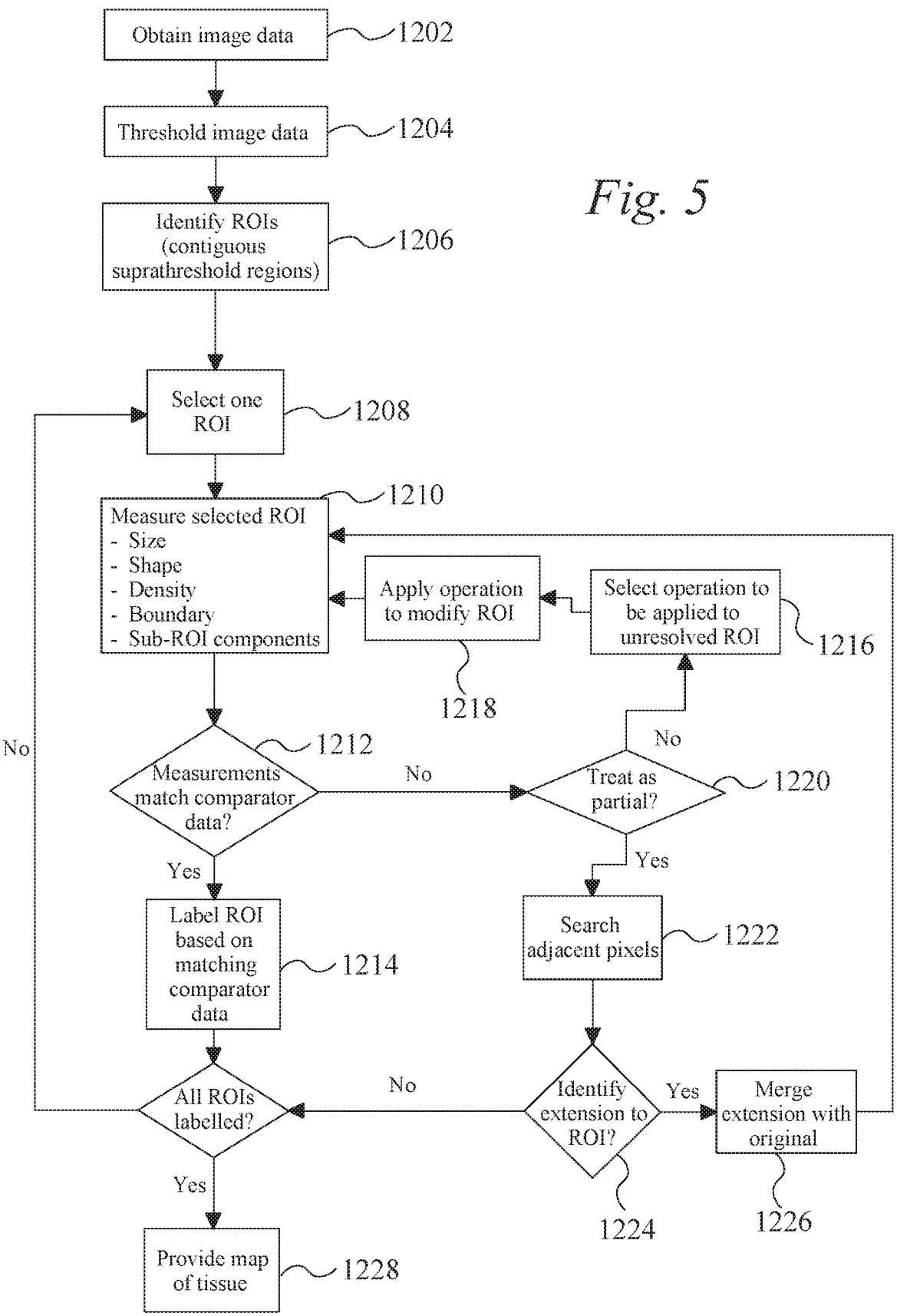
FIG. 5 illustrates a flow chart indicating an example of the method of FIG. 4.

FIG. 5 illustrates one example of a computer implemented image processing method such as that described above. This method can be applied to identify a tissue structure known, or expected, to be found in a particular tissue type. For example, if the method is applied to breast tissue it may be used to identify structures such as glands, ducts, lobules, or other structures which are found in such tissue. It may also be applied to other tissue types of course, in which case comparator data for different types of structures may be used.

As illustrated in FIG. 5, the computer obtains 1202 microscope image data for analysis. This microscope image data may be accompanied by descriptor data indicating type of tissue from which the microscope image was obtained. The microscope image data may also comprise data captured from a whole slide scan, for example in a 32 bit colour image. Such image data may be converted to optical density image data before further processing.

The computer then applies 1204 a threshold, for example an optical density threshold, to the image data to obtain first transformed image data. This first transformed image data is transformed by the application of a threshold in the sense that it is a two-state image of foreground (suprathreshold) and background (subthreshold) pixels, for example it may be binary data.

Structures in this first transformed image data are then classified by comparing them with comparator data. In this embodiment, to classify the structures (contiguous suprathreshold regions), the computer first identifies 1206 each contiguous group of suprathreshold pixels. This may be done by so called "blob extraction" methods such as connected component labelling. For example the computer may treat each suprathreshold pixel in turn, and for each such pixel identify the neighbours of that pixel which are also suprathreshold and identify (label) these as being part of the same contiguous group as that pixel. This process may be repeated iteratively until each contiguous group of pixels is labelled. These contiguous groups of pixels may each represent a structure (or part of a structure) in the underlying tissue from which the image data was obtained.

Each of these separate regions of interest (ROIs) is then compared with comparator data in an attempt classify that region of the underlying tissue. To perform this classification, a first one of these ROIs is selected 1208, and the computer determines 1210 at least one of the following quantitative image metrics:
  the size of the ROI,
  the shape of the ROI,
  the optical density of the ROI,
  the boundary of the ROI, and
  whether the ROI includes any identifiable sub-ROI components.

Other image metrics may also be used. To determine the size of the ROI the computer may count the number of pixels which make up the ROI. To determine the shape of the ROI the computer may use any one of a variety of different techniques, for example a template based matching method may be used, and/or the ratio of (1) the area of the ROI to (2) the square of the length of its boundary may be used to obtain information about the circularity of the ROI. Template based matching methods may comprise the computer applying a series of convolution kernels to the ROI, each having a different shape. In these cases, the shape of the ROI may be determined by identifying the convolution kernel which produces the output having the greatest total intensity. Other methods of identifying the shape of the ROI may be used.

The computer then obtains a set of (or sets of) comparator data values from the computer memory. For example the computer may use the descriptor data to retrieve, from its memory, comparator data associated with structures known or expected to be found in the tissue type from which the image data was obtained. For example if the descriptor indicates breast tissue, the computer may obtain comparator data associated with structures found in breast tissue, such as glands. It will be appreciated in the context of the present disclosure that glands only represents one type of structure, and their use here is merely an example. Similar processes may be carried out for nuclei, stroma, vessels, lumen, muscle and other structures.

The values of the quantitative image metrics (e.g. size, shape, density etc.) for the selected ROI are then compared 1212 with the comparator data. If the measured values of those metrics for that ROI match (e.g. to within a specified tolerance) the comparator data for a type of structure then that ROI is classified as being that type of structure. The computer labels 1214 the image pixels of that ROI as belonging to that type of structure.

In the event that the ROI does not match the comparator data, it is classified as an unresolved ROI. The computer then selects 1216 an operation to be applied to the unresolved ROI. The operation that is to be applied may be selected based on the characteristics of that ROI. The selected operation is then applied 1218 to the unresolved ROI obtain a modified ROI. For example, if the ROI is larger than a certain size then an erosion operation is applied to modify that ROI. This has the effect of modifying the transform provided by the initial thresholding operation, at least in so far as it relates to that ROI. Other ways of modifying the transform applied to the unresolved ROI may also be used.

The computer then attempts again to classify 1210 this newly modified ROI by calculating, for this modified ROI at least one of the following quantitative image metrics:
  the size of the modified ROI,
  the shape of the modified ROI,
  the optical density of the modified ROI,
  the boundary of the modified ROI, and
  whether the modified ROI includes any identifiable sub-ROI components.

As noted above, other image metrics may also be used. The data values obtained from these metrics in the modified ROI are then compared again against the comparator data. If the measured values of those metrics for that modified ROI match (e.g. to within a specified tolerance) the comparator data for a type of structure then that modified ROI is classified as being that type of structure. The computer labels 1214 the image pixels of that modified ROI as belonging to that type of structure.

In the event that the modified unresolved ROI also does not match the comparator data, the computer may determine 1220 whether to treat it as a partial structure. This may be done by identifying 1222 the image pixels in the original data which lie adjacent to (for example within a selected distance from a boundary of) the original unresolved ROI, and applying a revised threshold to those pixels. This may identify further suprathreshold groups of pixels around the ROI. The computer then merges 1226 these further suprathreshold regions with the original unresolved ROI (e.g. the ROI before the erosion operation described above) to create a merged ROI.

The computer then attempts again to classify 1210 this merged ROI by calculating, for this merged ROI at least one of the following quantitative image metrics:
  the size of the modified ROI,
  the shape of the modified ROI,
  the optical density of the modified ROI,
  the boundary of the modified ROI, and
  whether the modified ROI includes any identifiable sub-ROI components.

As noted above, other image metrics may also be used. The data values obtained from these metrics in the modified ROI are then compared again against the comparator data. If the measured values of those metrics for that merged ROI match (e.g. to within a specified tolerance) the comparator data for a type of structure then that modified ROI is classified as being that type of structure. The computer labels the image pixels of that merged ROI as belonging to that type of structure.

Once all the ROIs have been labelled in this way, the resulting labelled pixel data can be used to provide a map of the tissue which identifies which regions of the tissue are associated with different types of structures.

It will be appreciated in the context of the present disclosure that this is just one sequence of operations which may be used to identify structures using methods such as those described with reference to FIG. 4. This embodiment has been described with reference to an image transformation which uses a thresholding operation, which may be based on thresholding the optical density data. Other kinds of transformation may also be used.

For example, the image transformation used in the embodiment of either FIG. 4 or FIG. 5 may comprise an intensity transformation. This may reduce variations in the image data in one or more spatial frequency bands, for example it may comprise a band-pass filtering for example a smoothing (low pass filter), or an edge enhancement (high pass filter). In these embodiments modifying the transformation when ROIs do not match the comparator data may comprise varying the pass-band of the filter, for example using a different spatial frequency cut off, for example using a wider smoothing kernel. The intensity transformation may be configured to reduce the number of intensity levels in the image data. For example, it may comprise setting all values below a certain threshold to a floor value, for example a background value (e.g. a constant reference value, such as zero). The intensity transformation may comprise a binary thresholding operation in which pixels below the threshold are set to a first value (e.g. a logical "FALSE" value, for example 0), and pixels above the threshold are set to a second value (e.g. a logical "TRUE", for example 1). In these embodiments modifying the transformation comprises varying the threshold. The intensity transformation may comprise a morphological filter adapted to enhance and suppress selected image structures based on at least one of their size and shape. It will be appreciated in the context of the present disclosure that a morphological filter comprises a structuring element of selected size and shape. In these embodiments modifying the transformation may comprise varying at least one of the size and shape of the structuring element. Types of morphological filters comprise erosion, dilation, opening, closing. Modifying the transform may also comprise keeping the structuring element constant and varying the type of morphological filter that is to be applied.

The image transformation may also comprise histogram equalization. Histogram equalization may provide a method for modifying the dynamic range and contrast of an image by altering that image such that its intensity histogram has a desired shape. Such a method may employ a mapping function such as a non-linear and non-monotonic transfer functions to map between pixel intensity values in the input and output images. Accordingly—the output image contains a modified distribution of intensities (for example a more uniform, e.g. a flat histogram). By doing so, the perceived level of detail may be increased, and therefore it may provide image data in which it may be easier to identify structures. In these cases modifying the transformation may comprise modifying the mapping function used to transform the image data. Other image transformations may be applied as described below with reference to FIG. 7.

Additionally, it is envisaged that these further image analysis methods may be applied to image data obtained according to the methods set out above until a predetermined threshold number of structures has been identified within the image data.

The application of such further techniques may enable iterative image processing at multiple resolutions in digital pathology, and may, further, enable discrete tissue models and/or knowledge files to be constructed which contain information regarding tissue architecture against which new images can be compared. Additionally, these processes may be applied iteratively, with the resulting output data being refined and additional information identified in the image data with each iteration. Such an iteration process may be ceased when a particular confidence level is achieved, and/or may be stopped at a particular interval threshold. In an example, the iteration process may be stopped when a p-value of less than 10%, for example less than 5%, has been reached for identification of tissue. Further, the tissue models and/or knowledge files referenced above may be built through an iterative learning process. Data obtained by use of some or all of the techniques discussed above may also be combined with the original image data containing the Haematoxylin and Eosin stained tissue sample such that the data is mapped upon the image, such that a combination of the image data and the derived data are combined to provide a detailed representation of the content of the slide and/or tissue sample. This information may take the form of a modified image, and may be presented such that a user may obtain an 'augmented visualisation' of a tissue sample or image of a slide.

Figure 6:
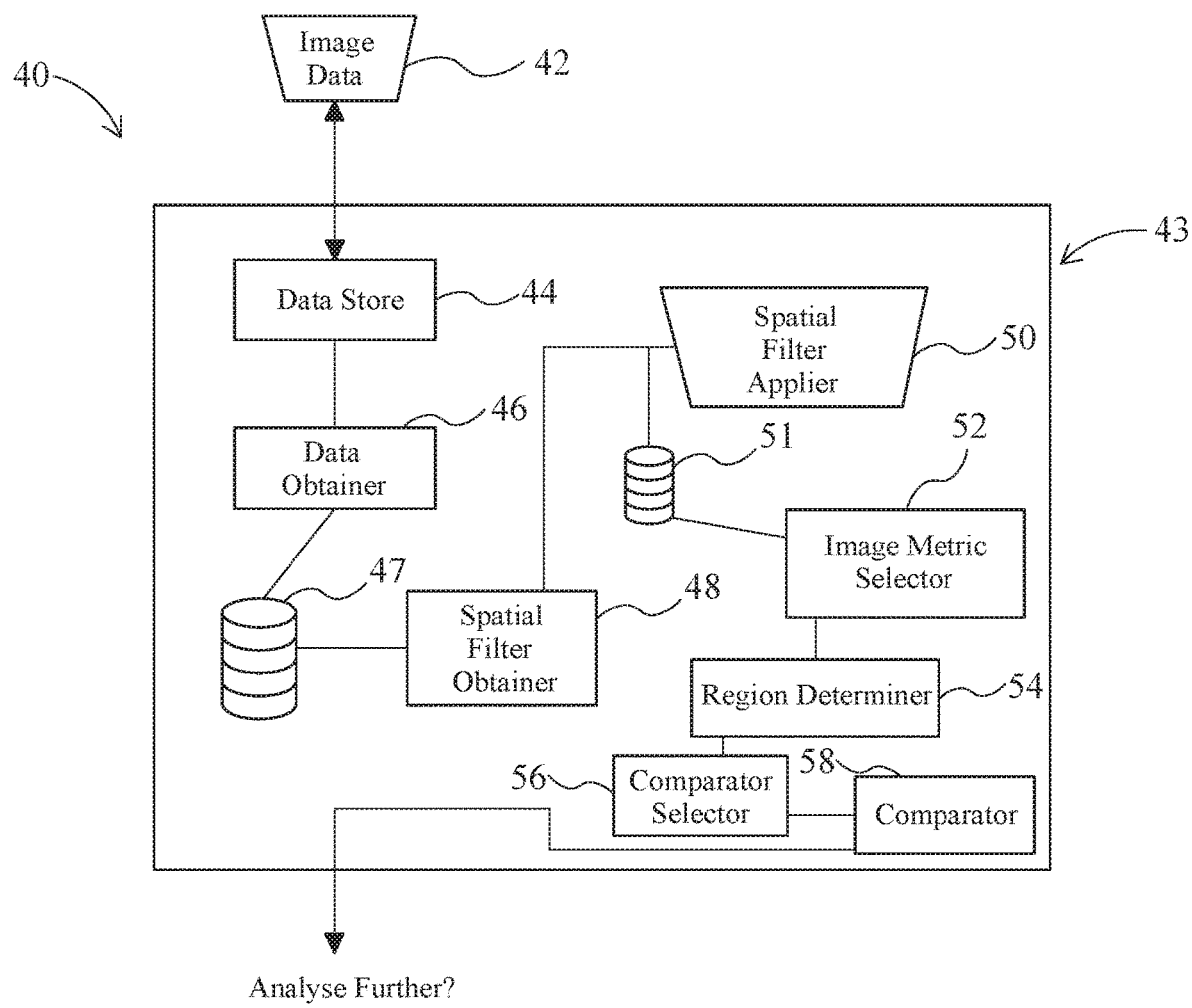
FIG. 6 shows a very schematic illustration of an image processing apparatus.

FIG. 6 illustrates an image processing apparatus 40 configured to perform a computer implemented image processing method. Other configurations of hardware may also be used to perform the same method, and methods similar to it.

The apparatus 40 may be further configured to provide at least one of (a) an augmented image comprising an indication of a result of at least one of said comparing steps and (b) a diagnostic indication of the presence of cancerous cells in the tissue based on a result of at least one of the said comparing steps.

The apparatus 40 of FIG. 4 comprises an image obtainer 42 and a processor 43. The processor 43 comprises an image data store 44, a descriptor data obtainer 46, a spatial filter store 47, a spatial filter selector 48, a spatial filter applier 50, a quantitative image store 51, a quantitative image metric selector 52, a data value region determiner 54, a comparator selector 56, and a comparator 58.

Although not shown in the drawings, each of these elements generally comprise computer readable storage and logic modules which may be realised in hardware such as combinations of logic gates and/or programmable logic such as field programmable gate arrays, FPGA, and/or application specific integrated circuits, and or by general purpose programmable processors in combination with appropriately configured firmware and software. One or more of these elements may be configured to provide efficient processing of data and/or matrices.

The data obtainer 42 comprises a data communication interface for obtaining microscope image data defining microscope slide images of haematoxylin and eosin stained tissue samples. Examples of data communication interfaces include Ethernet, and serial interfaces such as a universal serial bus interface—other examples of data communication interface maybe used.

Each of the elements of the apparatus 40 shown in FIG. 4 is coupled to communicate data and/or commands to one or more of the others. In particular, the data obtainer 42 is coupled to the processor 43, and therefore the image data store 44, the spatial filter applier 50, and the data value region determiner 54. The spatial filter selector 48 and the quantitative image metric selector 52 are connected to the image data store 44.

The data obtainer 42 comprises a data communication interface for obtaining microscope image data defining microscope slide images of haematoxylin and eosin stained tissue samples. Examples of data communication interfaces include Ethernet, and serial interfaces such as a universal serial bus interface—other examples of data communication interface maybe used.

The image data store 44 comprises data storage memory for storing image data which may contain either greyscale or three colour component data elements representing the overall colour of the or each image. This and other computer memory described herein may comprise volatile and/or non-volatile memory—for example random access memory, RAM, or on-chip cache memory, hard disc drives, HDD, or solid state drive, SSD.

The descriptor data obtainer 46 is adapted to obtain descriptor data from the image data store 44. The descriptor data may indicate a type of tissue from which the tissue sample originates, as set out above.

The spatial filter selector 48 is adapted to select, from the spatial filter store 47, a spatial filter or filters which may be configured to identify structured imaged data that describes structures having a spatial length scale in a selected range, as set out above. The spatial filter selector 48 may use the descriptor data obtained by the descriptor data obtainer 46 in selecting the spatial filter or filters.

The spatial filter applier 50 is configured to apply the selected spatial filter to the image data, and is further configured to identify a number of discrete spatial regions of the image, which comprises less than all of the area of the image.

The quantitative image metric selector 52 is configured to select a quantitative image metric from the quantitative image metric store 51, based upon descriptor data which is obtained from the image data store 44.

The data value determiner 54 is configured to apply the quantitative image metric or metrics selected by the selector 52, to obtain sample region data from the or each discrete spatial regions of the image as defined above.

The comparator selector 56 is configured to select a comparator set of tissue model data from the image data store 44, and the comparator 58 is configured to compare the sample region data against the comparator set of tissue model data.

In operation, the data obtainer 42 obtains a digital image of a microscope slide carrying a haematoxylin and eosin stained tissue sample from the image data store 44. The digital image slide may comprise a colour image of a stained tissue sample, or alternatively, may comprise a grayscale image of the stained tissue sample.

The descriptor data obtainer 46 then obtains descriptor data from the image data store 44 which may indicate a type of tissue from which the tissue sample originates. Then, the descriptor data is used by the spatial filter selector 48 to select a spatial filter or filters from the spatial filter store 47. The spatial filter or filters may be configured to identify structured imaged data that describes structures having a spatial length scale in a selected range.

The spatial filter applier 50 then applies the selected filter to the image data to identify a subset of image data that defines a number of discrete spatial regions of the image wherein the discrete spatial regions comprise less than all of the area of the image. The quantitative image metric selector 52 then selects from the quantitative image metric store 51, a set of quantitative image metrics based on the descriptor data.

The data value determiner 54 then applies the or each quantitative image metric, for each discrete spatial region, to obtain sample region data value for the or each quantitative image metric based on the subset of image data associated with the or each discrete spatial region.

The comparator selector 56 is then obtains at least one comparator set of tissue model data from the image data store 44, with each comparator set associated with a different corresponding comparator tissue structure and each comparator set comprises data values of the set of quantitative image metrics for the corresponding comparator tissue structure.

The comparator 58 then compares the sample region data value for each discrete region with the at least one comparator set and in the event that the sample region data value for the or each discrete region matches the comparator set, the processor determines, based on an identity of the corresponding comparator tissue structure, whether to analyse further the or each discrete region.

Figure 7:
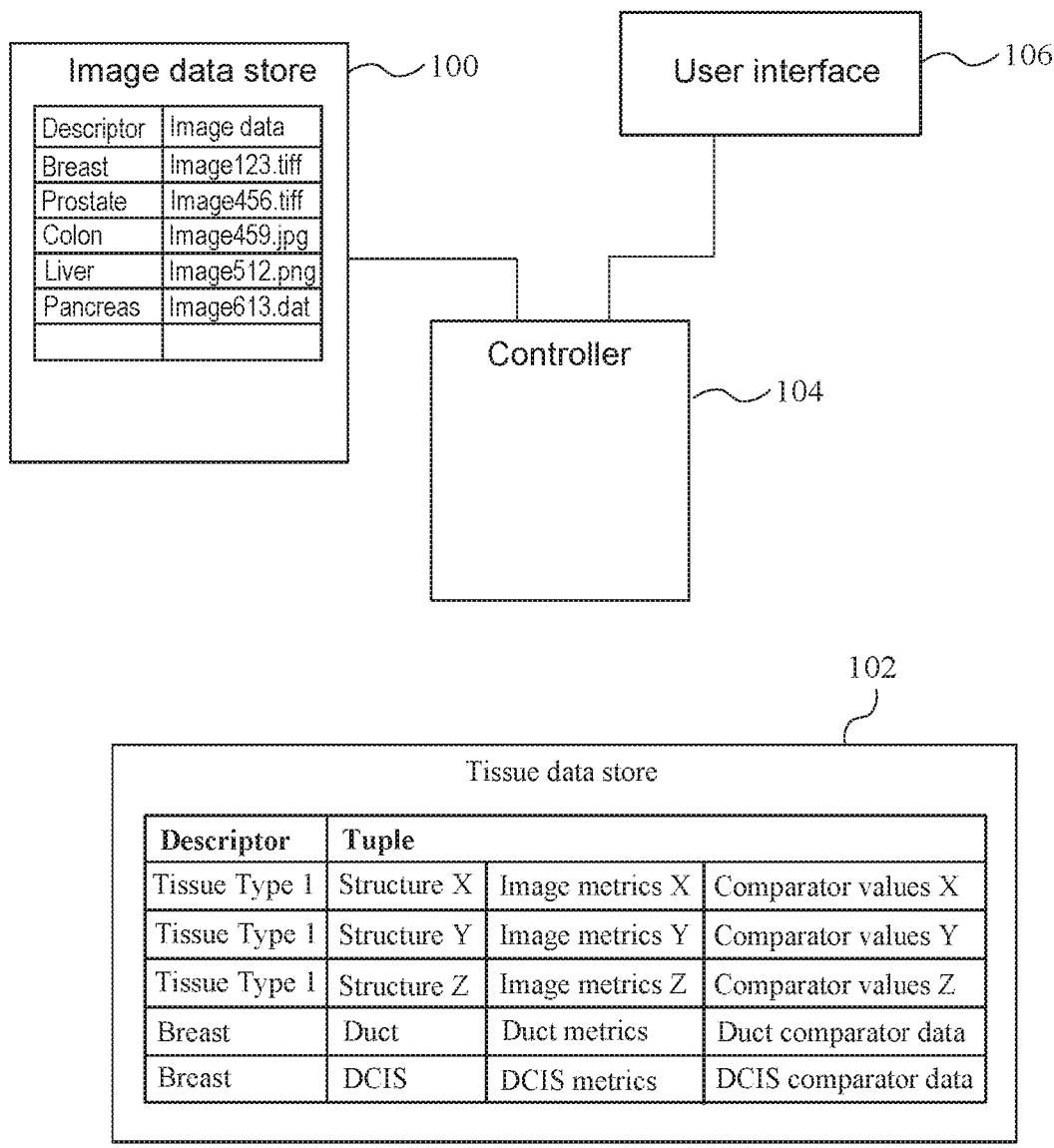
FIG. 7 is a functional block diagram of an image processing apparatus.

FIG. 7 relates to an apparatus configured to perform a computer implemented microscope image processing method for identifying structures in a digital microscope image. In this method a first image data set is obtained from a digital microscope image.

An image transformation is then applied to that first image data to obtain second image data. Structures in this second image data are then classified by comparing them with comparator data to identify them as belonging to one of a number of structures known (or expected) to be found within the tissue type.

In the event that unclassified structures remain in the second image data, the image transformation is modified, and applied again to at least the part of the image data which includes the unclassified structures. This provides a third image data set. Structures in this third image data can then be classified by comparing them with the comparator data.

This process of attempted classification followed by modification of the image transform, followed by reattempted classification of the newly transformed (unclassified) image structures can be repeated until all structures in an image (or an acceptable proportion of those structures) have been properly classified.

The image transformations used in this method may include contrast stretching, spatial filtering (for example morphological filtering), histogram equalisation, colour channel deconvolution, and other transformations. A particular embodiment of this method will now be described in which the image transformation comprises a morphological filter. It will be appreciated however that any of these other transform operations may also be used.

The embodiment illustrated in FIG. 7 comprises an image data store 100, a tissue data store 102, a controller 104, and a user interface. The controller 104 is coupled to communicate data to and from each of the image data store 100, the tissue data store 102, and the user interface 106.

The image data store 100 and the tissue data store 102 both comprise volatile and/or non-volatile data memory for storage and retrieval of digital image data and a data interface to enable data to be read from and written to that memory. Each is coupled to the controller 104 to enable the controller 104 to obtain image data from the image data store 100, and to obtain tissue data such as quantitative image metrics and comparator data from the tissue data store 102. The image data store 100 is also configured to store, for each item of image, a corresponding descriptor of the tissue type from which that image originates. The tissue data store 102 stores a number of descriptors, labels, each corresponding to a different tissue type. Examples of such tissue types include breast tissue, prostate tissue, lung tissue, pancreatic tissue and other types of tissue. The tissue data store 102 also stores, for each descriptor, a set of tuples. Each tuple provides an association between (a) a structure known (or expected) to be found in the tissue type identified by the descriptor, (b) a set of quantitative image metrics, and (c) a set of comparator data values indicating expected values of those image metrics in that structure.

The controller 104 comprises processing logic, configured to read and write data to and from storage in the image data store 100 and the tissue data store 102. The controller 104 is also operable to apply an image transformation to image data obtained from the image data store 100. That image transformation comprises a morphological filter having a structuring element of a selected shape and size, but as explained above this is just one example of a type of transformation. The controller 104 is operable to vary the size and/or shape of that structuring element. The controller 104 is also configured to obtain image data and a descriptor of that image from the image data store 100. The controller 104 is configured to use that descriptor to select the relevant set of tuples from the tissue data store 102. The controller 104 is further operable to select one of those tuples, (e.g. associated with a particular structure known or expected to be found in the tissue type) and thereby to obtain a set of quantitative image metrics. The controller 104 is operable to apply these quantitative image metrics to the image data, and by evaluating those metrics to obtain a set of sample data values which characterise the image data. These sample data values can be thought of as a type of fingerprint which can be used for inferring the structure from which the image data, or parts of that image data, might originate. Accordingly, the controller 104 is configured to compare the sample data values with the comparator data values which are stored in the tuple for that image structure. This enables the controller 104 to determine the degree to which the fingerprint of the image data might match the fingerprint of the structure associated with that tuple. Depending on the nature of the image metric, that comparison might be performed by determining whether the data obtained by evaluating any particular one of the metrics falls within a selected range of values for that metric as defined by the relevant comparator data.

In operation, the controller 104 reads image data and a corresponding descriptor from the image data store 100. The controller 104 then applies a morphological filter to this first image data to transform the data into second image data. The controller 104 then identifies, in the tissue data store 102, the set of tuples associated with the descriptor of the image data—e.g. it uses the descriptor as an index to look up the relevant set of tuples.

The controller 104 then selects a first structure from amongst the set of structures identified by that set of tuples. The controller 104 then evaluates the quantitative image metrics (listed in the tuple for that first structure) by applying those metrics to the second image data. The controller 104 then compares the data values (obtained by evaluating these metrics for the second image data) with the comparator data stored in the tuple for the first structure. In the event that the data values associated with one or more parts of the second image data match the comparator data for a given structure, the controller 104 can classify those one or more parts as belonging to that structure. The controller 104 can then perform the same process for each of the structures associated with the descriptor until either all of the image data has been classified, or all of the structures associated with that descriptor have been checked.

In the event that, after this procedure, one or more areas of the second image data remain unclassified, the controller 104 modifies the morphological filter, for example by changing the size and or shape of the filter's structuring element, and then applies the modified filter to the unclassified areas of the first image data. By applying this modified image transform, the controller 104 obtains third image data. The controller 104 then goes through the process of classifying that data by evaluating the quantitative image metrics associated with each structure and performing the comparisons explained above. In the event that some of the image data remains unclassified at the end of this procedure, the controller 104 can further modify the morphological filter and repeat the process. This can be done iteratively until all but an acceptable amount of the data has been classified.

It will be appreciated in the context of the present disclosure that the process described above is merely exemplary, and it may be varied in a number of ways. For example, a single structure may be associated with each tissue type descriptor, and so the set of tuples may comprise only a single tuple. In addition, each structure may only be associated with a single quantitative image metric.

Examples of suitable quantitative image metrics one or more items selected from the list comprising: a frequency domain metric, a texture metric such as a Gray-Level Co-Occurrence Matrix ('GLCM') metric, an optical density, a colour, and any other suitable metric. These metrics may have the features and be applied, in the manner explained above.

The tissue data is described as being stored in tuples, but any data structure capable of storing an association between elements of data may be used. Examples include lists, linked lists, arrays, look-up tables, and the like.

Other variations are contemplated. For example, in some embodiments the image transform may not be provided by a morphological filter. For example an image transform such as a smoothing or sharpening filter may be used. This kind of transform may enhance and/or attenuate selected spatial frequency components of an image. In these embodiments, modifying the image transformation may comprises modifying the degree of attenuation or enhancement applied to one or more of those spatial frequency components and/or causing the filter to attenuate or enhance different selected spatial frequency components. This may be achieved by varying a transfer function of the filter.

As another example, the controller 104 may be configured to apply different types of image transform. For example, a morphological filter might be applied first, then if all data cannot be classified using the filtered data obtained by applying that filter, a different type of image transform may be applied. The image transform may be selected based on at least one of: (a) at least one quantitative image metric of the image data; (b) descriptor data indicating the type of tissue from which the microscope image originates. For example—if the descriptor data indicates that the tissue is breast tissue, and a spatial frequency metric of the data indicates the presence of structures having a length scale in a band which corresponds to ducts and lobules, the controller 104 may select the morphological filter (or other image transform) to identify these structures. For example, the size and shape of the structuring element of the morphological filter may be selected to match the shape and/or size of a duct or lobule. This is of course merely exemplary and the image transform may be selected based on any other known characteristic of structures known (or expected) to be present in the tissue identified by the descriptor.

As noted already, many different types of image transform may be used for the method explained with reference to FIG. 7. For example, the image transform may comprise an intensity transformation adapted to modify the intensity of at least one colour channel of the image data to which it is applied.

The image transform may comprise a histogram transform, for example an operation configured to modify the frequency distribution of image pixel values. For example this may be a histogram equalisation—i.e. an operation which increases the uniformity of the frequency distribution of image pixel values. Such operations may comprise applying a mapping function to the intensity of at least one colour channel of the image data to which it is applied. In these examples, modifying the image transformation may comprise modifying this mapping function. Likewise, the image transformation may comprise a contrast stretching operation. Examples of contrast stretching operations comprise applying a linear transformation to the intensity of at least one colour channel of the image data to which it is applied. As will be appreciated a linear transformation may comprise an additive term, and a linear scaling. Modifying such a transform may comprise changing the value (or sign) of the additive term and/or changing the value (or sign) of the linear scaling.

It will also be appreciated in the context of the present disclosure that the image data referred to herein may originate from any one of a plurality of different classes of imaging system. These systems may each use different image acquisition protocols, and different types of optics. For example, some systems acquire a series of monochrome images each using a different one of a series of different colour filters. The resulting monochrome images can then be combined to provide a colour image if a sample in discrete, well-defined colour bands. Other systems use colour cameras in combination with multi-band filters. Such filters may have for example three predefined colour pass-bands so as to generate colour images in a single shot. The pass bands may be selected based on the characteristics of the sample or analysis technique. Some examples of whole-slide imaging systems include the Aperia ScanScope FL (available from Aperio, Vista, Calif.), the Leica SCN400F (available from Leica Biosystems, Richmond, Ill.). The 3DHistech P250 (available from 3DHistech, Budapest, Hungary) is an example of this kind of scanner. Other examples of whole-slide imaging systems include the Omnyx VL140 (available from Omnyx, Pittsburgh, Pa.), the Olympus VS120 (available from Olympus Corporation, Tokyo, Japan), and the Philips UFS System (available from Philips Digital Pathology Solutions, Best, The Netherlands). Yet further systems exist and no doubt will be developed in the future—embodiments of the invention may permit the processing of, and comparison between, image data originating from any one or more of such systems.

Whole slide microscope images may have a resolution of a few hundred nanometres, for example 250 nm. The tissue samples themselves may each be ten millimetres across or more, for example about 15 mm by 15 mm. Whole slide images of such samples may comprise at least $10^8$ pixels, for example at least $10^9$. In some embodiments whole slide images comprise $10^8$ to $10^{10}$ pixels.

To the extent that certain methods may be applied to the living human or animal body, it will be appreciated that such methods may not provide any surgical or therapeutic effect. In addition, it will be appreciated that such methods may be applied ex vivo, to tissue samples that are not part of the living human or animal body. For example, the methods described herein may be practiced on meat, tissue samples, cadavers, and other non-living objects.

With reference to the drawings in general, it will be appreciated that schematic functional block diagrams are used to indicate functionality of systems and apparatus described herein. It will be appreciated however that the functionality need not be divided in this way, and should not be taken to imply an particular structure of hardware other than that described and claimed below. The function of one or more of the elements shown in the drawings may be further subdivided, and/or distributed throughout apparatus of the disclosure. In some embodiments the function of one or more elements shown in the drawings may be integrated into a single functional unit.

The above embodiments are to be understood as illustrative examples. Further embodiments are envisaged. It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

For example in some embodiments the methods described herein comprise applying a morphological filter to the image data in the event that it has been determined that one or more discrete region of that image data is to be further analysed. For example such a morphological filter may only be applied to regions that have been selected to be further analysed. Such a morphological filter may have a structuring element selected to provide cell nuclei data identifying cell nuclei. For example, the structuring element may be circular and may have a diameter of less than 20 micron, for example less than 10 micron. This cell nuclei data may enable it to be determined whether the at least one discrete region comprises cancerous cells. For example such methods may comprise determining a metric of at least one of nuclear shape and nuclear size from the cell nuclei data, and comparing the at least one of nuclear shape and nuclear size with comparator data to determine whether the at least one discrete region comprises cancerous cells. Such methods may further comprise obtaining cell boundary data that identifies cell boundaries in the or each discrete region and/or determining whether the at least one discrete region comprises cancerous cells based on the cell boundary data. For example this may comprise determining at least one of cell shape and cell size from the cell boundary data, and comparing the at least one of cell shape and cell size with comparator data to determine whether the at least one discrete region comprises cancerous cells.

In some examples, one or more memory elements can store data and/or program instructions used to implement the operations described herein. Embodiments of the disclosure provide tangible, non-transitory storage media comprising program instructions operable to program a processor to perform any one or more of the methods described and/or claimed herein and/or to provide data processing apparatus as described and/or claimed herein.

The activities and apparatus outlined herein may be implemented with fixed logic such as assemblies of logic gates or programmable logic such as software and/or computer program instructions executed by a processor. Other kinds of programmable logic include programmable processors, programmable digital logic (e.g., a field programmable gate array (FPGA), an erasable programmable read only memory (EPROM), an electrically erasable programmable read only memory (EEPROM)), an application specific integrated circuit, ASIC, or any other kind of digital logic, software code, electronic instructions, flash memory, optical disks, CD-ROMs, DVD ROMs, magnetic or optical cards, other types of machine-readable mediums suitable for storing electronic instructions, or any suitable combination thereof.

In some examples the functionality of the computer and/or the processor may be provided by digital logic, such as field programmable gate arrays, FPGA, application specific integrated circuits, ASIC, a digital signal processor, DSP, or by software loaded into a programmable processor. The functionality of the processor and its programs may be provided in a single integrated unit, or it may be distributed between a number of processors, which may be arranged to communicate over a network, such as "cloud" computing. This may enable, for example, the processing steps of the method to be performed at a device (or devices) that are remote from the image capture and the image analysis.

In the context of the present disclosure other examples and variations of the devices and methods described herein will be apparent to a person of skill in the art. Other examples and variations are within the scope of the disclosure, as set out in the appended claims.

The invention claimed is:
1. A computer implemented image processing method comprising:
obtaining microscope image data defining a microscope slide image of a haematoxylin and eosin stained tissue sample, wherein the microscope slide image data comprises a plurality of image pixels;
obtaining descriptor data indicating a type of tissue from which the tissue sample originates;
selecting, based on the descriptor data, a spatial filter configured to identify structured image data that describes structures having a spatial length scale in a selected range;
applying the selected filter to the image data to identify a subset of image data that defines a number of discrete spatial regions of the image wherein the discrete spatial regions comprise less than all of the area of the image;
selecting, from a data store, a set of quantitative image metrics wherein the quantitative image metrics are selected based on the descriptor data,
determining, for each discrete spatial region, a sample region data value for each of the set of quantitative image metrics based on the subset of image data associated with the or each discrete spatial region,
using the descriptor data to select, from the data store, at least one comparator set of tissue model data values, wherein each comparator set is associated with a different corresponding comparator tissue structure and each comparator set comprises data values of the set of quantitative image metrics for the corresponding comparator tissue structure;
comparing the sample region data value for each discrete region with the at least one comparator set;
in the event that the sample region data value for the or each discrete region matches the comparator set, determining based on an identity of the corresponding comparator tissue structure, whether to further analyse the or each discrete region
applying a first morphological filter to the image data in the or each discrete region in the event that the or each discrete region is to be further analysed, wherein the morphological filter has a structuring element selected to provide cell nuclei data identifying cell nuclei;
determining, based on the cell nuclei data, a metric of at least one of: nuclear shape, nuclear area, and shape factor and comparing said metric with comparator data to determine whether it is likely that the or each at least one discrete region comprises cancerous cells.

2. The method of claim 1 in which the spatial filter comprises a morphological filter having a structuring element selected based on the descriptor data.

3. The method of claim 1 wherein the set of quantitative image metrics comprise a metric based on at least one of:
   (a) optical density in the or each discrete region;
   (b) spatial frequency data in a selected range of spatial frequencies in the or each discrete region;
   (c) texture data in the or each discrete region; and
   (d) at least one metric of tissue morphology on a length scale selected based on the descriptor data.

4. The method of claim 1 wherein the comparator structure comprises a carcinoma in situ.

5. The method of claim 4 wherein in the event that the or each discrete region is not to be further analysed, the or each discrete region is excluded from subsequent analysis of the image data.

6. The method of claim 5 comprising obtaining data values of said set of quantitative image metrics from a plurality of microscope slide images, selecting a sequence of the plurality of microscope slide images based on the data values of the at least one of said sets of quantitative image metrics, for example comprising presenting the plurality of microscope slide images to a human operator in the selected sequence.

7. The method of claim 6 wherein the image data comprises optical density data.

8. A diagnostic apparatus configured to perform the method of claim 6, for example configured to provide at least one of (a) an augmented image comprising an indication of a result of at least one of said comparing steps and (b) a diagnostic indication of the presence of cancerous cells in the tissue based on a result of at least one of said comparing steps.

9. An apparatus comprising:
   an image obtainer configured to obtain microscope image data and to provide the data to the image processor, wherein the image data defines a microscope slide image of a haematoxylin and eosin stained tissue sample and the microscope slide image data comprises a plurality of image pixels; and
   a processor, for performing operations on the image data, and configured to:
   obtain descriptor data indicating a type of tissue from which the tissue sample originates;
   select, based on the descriptor data, a spatial filter configured to identify structured image data that describes structures having a spatial length scale in a selected range;
   apply the selected filter to the image data to identify a subset of image data that defines a number of discrete spatial regions of the image wherein the discrete spatial regions comprise less than all of the area of the image;
   select, based on the descriptor data, a set of quantitative image metrics;
   determine, for each discrete spatial region, a sample region data value for each of the set of quantitative image metrics based on the subset of image data associated with the or each discrete spatial region,
   obtain at least one comparator set of tissue model data values, wherein each comparator set is associated with a different corresponding comparator tissue structure and each comparator set comprises data values of the set of quantitative image metrics for the corresponding comparator tissue structure;
   compare the sample region data value for each discrete region with the at least one comparator set; and
   wherein the processor is configured so that, in the event that the sample region data value for the or each discrete region matches the comparator set, the processor determines, based on an identity of the corresponding comparator tissue structure, whether to further analyse the or each discrete region; and the processor is configured to:
   apply a first morphological filter to the image data in the or each discrete region in the event that the or each discrete region is to be further analysed, wherein the first morphological filter has a structuring element selected to provide cell nuclei data identifying cell nuclei; and
   determine, based on the cell nuclei data, a metric of at least one of: nuclear shape, nuclear area, and shape factor and comparing said metric with comparator data to determine whether it is likely that the or each at least one discrete region comprises cancerous cells.

10. The apparatus of claim 9 wherein the structuring element of the first morphological filter is circular and has a diameter of less than 20 micron, for example wherein the processor is configured to augment the image data based on the at least one of nuclear shape and nuclear size.

11. The apparatus of claim 9 comprising wherein the processor is configured to augment the image data based on cell boundary data that identifies cell boundaries in the or each discrete region, for example wherein the processor is configured to determine the cell boundary data from gradient image data of the or each discrete region, for example based on watershedding.

12. The apparatus of claim 11 wherein the cell boundary data comprises at least one of cell shape and cell size.

13. The apparatus of claim 9 wherein the processor is configured to obtain data values of said set of quantitative image metrics from a plurality of microscope slide images, and in which augmenting the image data comprises selecting a sequence of the plurality of microscope slide images based on the data values of the at least one of said sets of quantitative image metrics, for example wherein the processor is configured to present the plurality of microscope slide images to a human operator in the selected sequence.

14. The apparatus of claim 9 wherein the processor is configured to augment the image data by highlighting the or each discrete region.

15. The apparatus of claim 9 configured to provide at least one of (a) an augmented image comprising an indication of a result of at least one of said comparing steps and (b) a diagnostic indication of the presence of cancerous cells in the tissue based on a result of at least one of said comparing steps.

* * * * *